United States Patent
Kim-Whitty

(10) Patent No.: US 9,967,553 B1
(45) Date of Patent: May 8, 2018

(54) ENHANCED TRANSPARENT DISPLAY SCREEN FOR MOBILE DEVICE AND METHODS OF OPERATION

(71) Applicant: SK COMMERCIAL CONSTRUCTION, INC., Belton, TX (US)

(72) Inventor: Suk K. Kim-Whitty, Belton, TX (US)

(*) Notice: Subject to any disclaimer, the term of this patent is extended or adjusted under 35 U.S.C. 154(b) by 0 days. days.

(21) Appl. No.: 15/477,124

(22) Filed: Apr. 3, 2017

Related U.S. Application Data

(60) Provisional application No. 62/420,544, filed on Nov. 10, 2016.

(51) Int. Cl.

| | |
|---|---|
| A63F 13/2145 | (2014.01) |
| H04N 13/04 | (2006.01) |
| H04N 13/00 | (2018.01) |
| H04N 13/02 | (2006.01) |
| A63F 13/25 | (2014.01) |
| G06Q 30/02 | (2012.01) |
| G06F 3/0354 | (2013.01) |
| G06F 3/041 | (2006.01) |

(52) U.S. Cl.
CPC ..... *H04N 13/0409* (2013.01); *A63F 13/2145* (2014.09); *A63F 13/25* (2014.09); *G06Q 30/0267* (2013.01); *H04N 13/0022* (2013.01); *H04N 13/0207* (2013.01); *H04N 13/0422* (2013.01); *H04N 13/0497* (2013.01); *A63F 2300/66* (2013.01); *G06F 3/03547* (2013.01); *G06F 3/0414* (2013.01); *G06F 2203/04108* (2013.01)

(58) Field of Classification Search
CPC ............................ A63F 13/2457; G06F 1/1647
See application file for complete search history.

(56) References Cited

U.S. PATENT DOCUMENTS

| | | | |
|---|---|---|---|
| 7,198,341 B1* | 4/2007 | Rast ....................... | B41J 3/4071 345/179 |
| 2014/0085282 A1* | 3/2014 | Luebke ................... | G06F 3/147 345/207 |
| 2014/0378183 A1* | 12/2014 | Xiong ............... | H04M 1/72522 455/556.1 |
| 2015/0355729 A1* | 12/2015 | Park ...................... | G06F 3/1446 345/173 |

\* cited by examiner

*Primary Examiner* — Omkar Deodhar
(74) *Attorney, Agent, or Firm* — Hulsey, P.C.

(57) ABSTRACT

Enhanced transparent display screen for electronic mobile device and method of operation. The display may include a dual display screen varying in translucency. The dual display screen may be a transparent organic light emitting display, and the non-transparent display may be a liquid crystal display. For gaming and photo applications, the invention responds to different level of pressure on touchscreen to access different layers of objects in parallax image or bottom layer of transparent display screen. Advertisements delivered on the electronic mobile devices by virtue of a mobile app are displayed on the electronic device screen outside the confines or borders of the mobile app. Advertisements are viewed on a rear display screen to non-users of the electronic mobile device. The dual screen may be touch screen with proximity detection and allow for multi-player gaming.

11 Claims, 10 Drawing Sheets

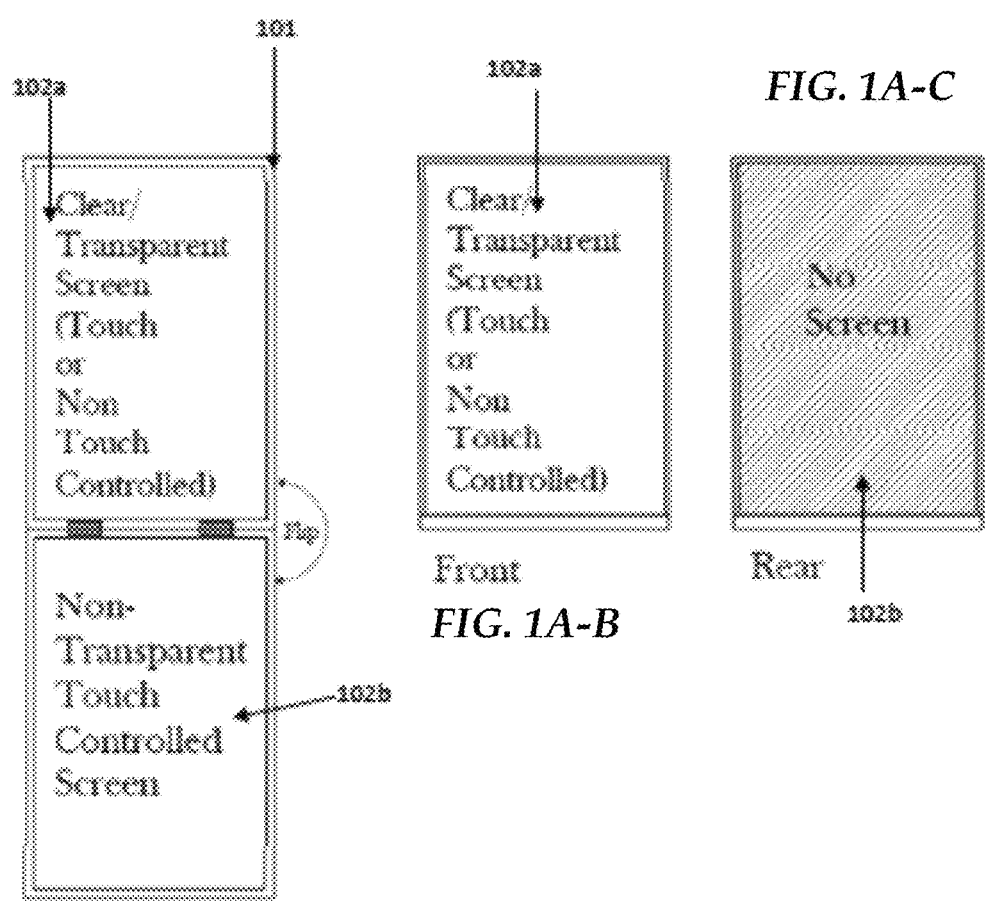

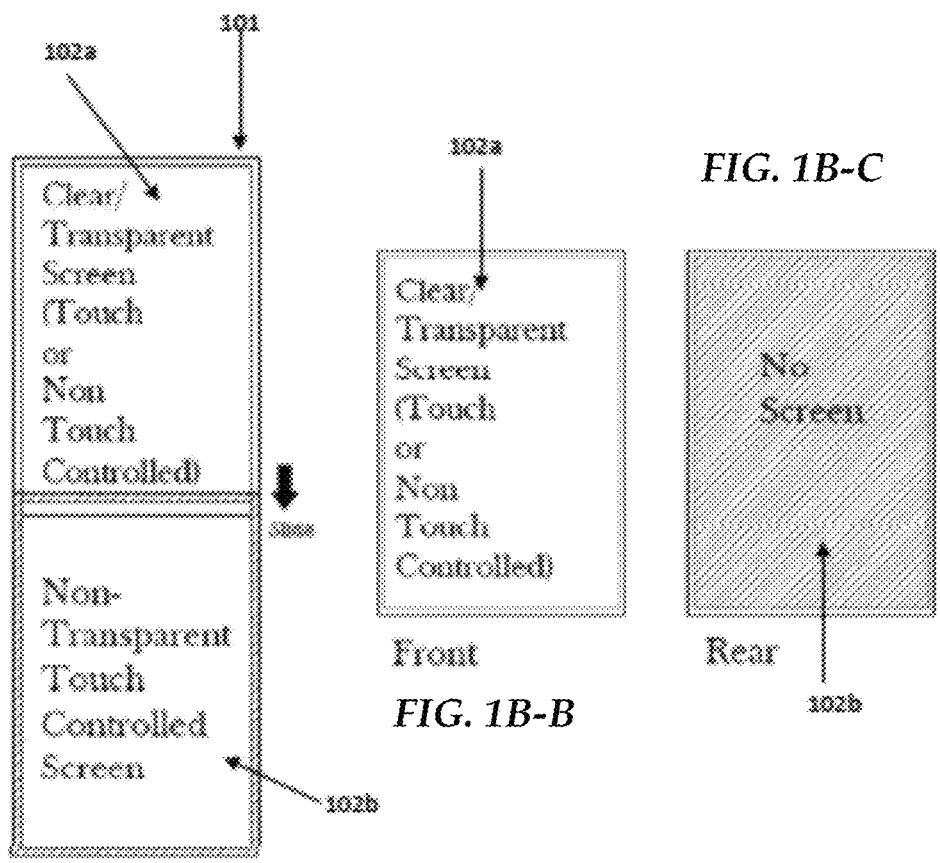
FIG. 1B-A
FIG. 1B-B
FIG. 1B-C

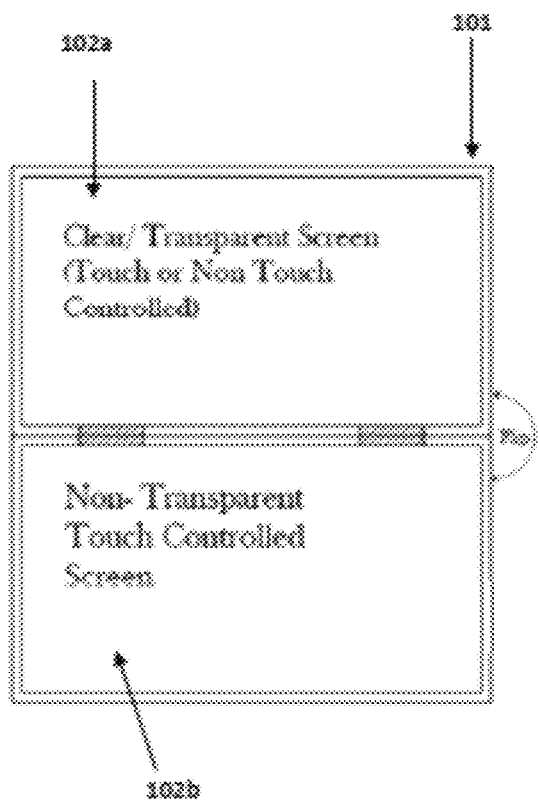
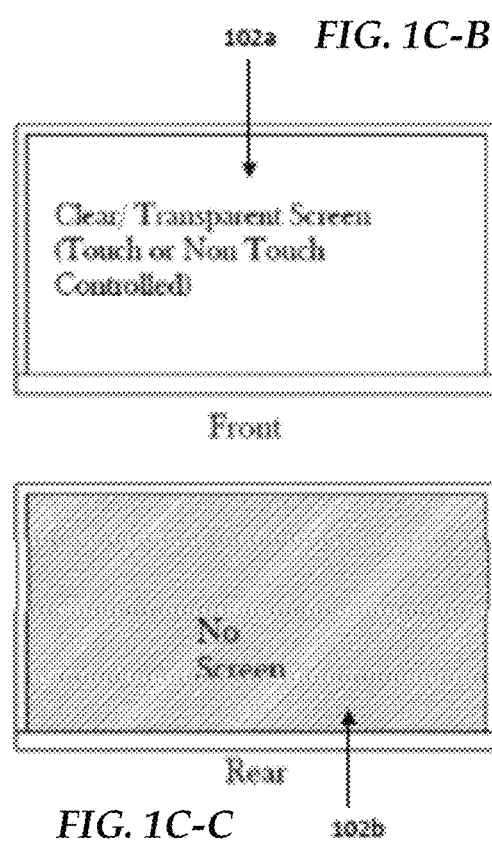
FIG. 1C-A
FIG. 1C-B
FIG. 1C-C

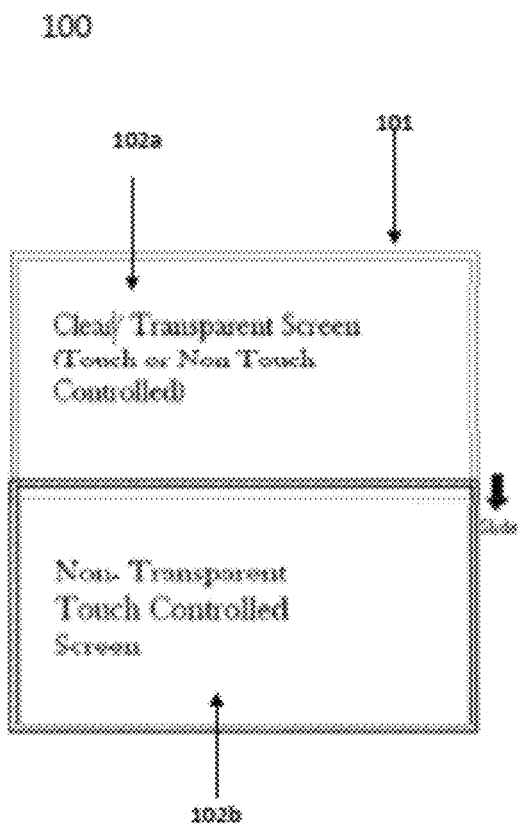
FIG. 1D-A
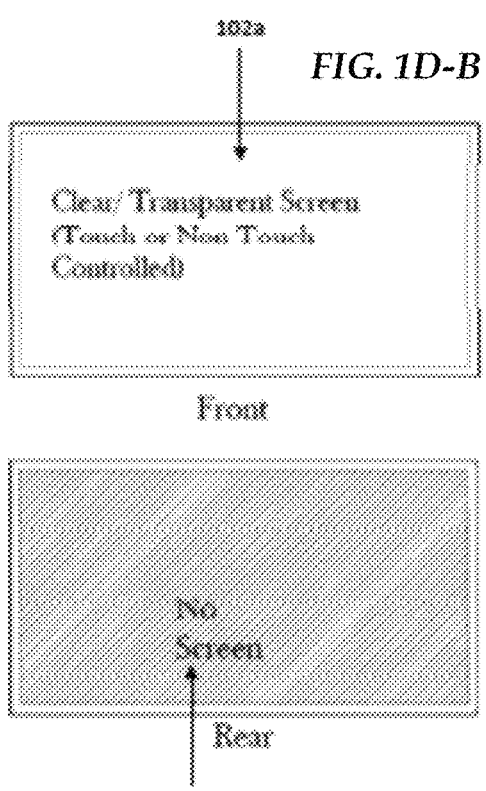
FIG. 1D-B
FIG. 1D-C

100

100

ENHANCED TRANSPARENT DISPLAY SCREEN FOR MOBILE DEVICE AND METHODS OF OPERATION

CROSS REFERENCE TO RELATED APPLICATIONS

This application claims benefit to the Provisional Application No. 62/420,544 filed on Nov. 10, 2016 and Non-Provisional application Ser. No. 15/464,231 filed on Mar. 20, 2017 as is expressly incorporated herein by reference.

This application further claims the benefit of the following Non-Provisional applications, all of which are here expressly incorporated by reference:

Ser. No. 15/464,231 entitled "METHOD AND SYSTEM FOR ADVERTISING AND SCREEN IDENTIFICATION USING A MOBILE DEVICE TRANSPARENT SCREEN," filed on Mar. 20, 2017;

Ser. No. 15/477,301 entitled "COLOR ANALYSIS AND CONTROL USING AN ELECTRONIC MOBILE DEVICE TRANSPARENT DISPLAY SCREEN," filed on Apr. 3, 2017; and Ser. No. 15/477,131 entitled "METHOD AND SYSTEM FOR CORRELATING ANATOMY USING AN ELECTRONIC MOBILE DEVICE TRANSPARENT DISPLAY SCREEN," filed on Apr. 3, 2017.

FIELD OF THE INVENTION

The present disclosure relates generally to electronic mobile devices with an enhanced transparent display screen. The disclosure further relates to electronic mobile devices with improved display screens and technical capabilities.

BACKGROUND OF THE ART

Enhancement of transparent display screens by utilizing layers of transparent display screen to show advertisement while front electronic mobile device is held against a user's ear or held in front of the user is a rising technology.

Advertisement and displaying of information on electronic devices has been a rising industry and sales marketing tool in today's business market. These electronic devices, e.g. computers, mobile devices (smartphone and/or tablets), have been increasingly employed in the advertising screen or banner. The vast majority of advertising platforms and models utilizing such electronic devices randomly provide advertisements with web page links, email links, and contemporaneously with mobile applications and games, or via spam in email.

Examples of advertising platforms utilizing mobile devices for advertisement are provided herein below.

U.S. Pat. No. 9,367,093 to Pence discloses a method and system for displaying images on a transparent display of an electronic device. The display includes one or more display screens as well as a flexible circuit for connecting the display screens with internal circuitry of the electric device. Furthermore, the display screens allow for overlaying of images over real world viewable objects, as well as a visible window to be present on an otherwise opaque display screen. Additionally, the display includes active and passive display screens that are utilized based on images to be displayed.

U.S. Patent Application Publication No. 20140188614 to Badenhop discloses a mobile billboard messaging icon displaying messages related to a user's preferences from an advertiser's on the display of a user's devices, such as Smartphone or tablet, having internet connectivity, location technology, and logic means for determining when the user device is in a given vicinity of the advertiser's location. The coordinate location of the device is used to identify advertiser's locations within a preselected distance that correlate with user's preferences. Where a correlation is found, at least one message from the advertiser is displayed on the Smartphone or tablet device. The message is triggered when the device enters within the given radii from the advertiser. When triggered, the messaging icon provides relevant real-time promotions, deals and coupons for purchase of goods and services of the advertisers or sponsors related to the user preferences. The mobile billboard displays target messages based on both the user's specific preferences and the user's geographical real-time location.

U.S. Patent Application Publication No. 20140188616 to Badenhop discloses a mobile billboard messaging app and non-transitory computer readable electronic storage medium. The method includes a computer database electronically storing merchant/advertiser and user information in communication with a software application running in a mobile device of the user. The mobile device has GOS technology, a display screen and Internet connectivity. The method displays on the user's device messages from an advertiser that are logically related to user preferences when the user device is in a given location radii. Where a correlation is found, at least one message from the advertiser is displayed. The message is triggered when the device enters within the given radii from the advertiser. When triggered, the messaging app provides relevant real-time promotions, deals and coupons related to the user preferences. The mobile billboard displays target messages based on both the user's preferences and the user's geographical real-time location.

U.S. Patent Application Publication No. 20150039440 to Doumet discloses a method and system for displaying images on ads delivered to mobile devices by virtue of a mobile app executing on the device are displayed on the device screen outside the confines or borders of the mobile app. This enables app developers to display ads through their apps to app users wherein the ads are displayed outside the confines of the actual app as displayed on the device. That is, the ad may be displayed as what may be characterized as a 'regular non-app generated' ad, such as on the device's home or lock screen (display areas not normally associated with an app). In this manner, clutter is decreased within mobile apps that would otherwise be caused by the ads. Consequently, advertisers are more likely to pay higher rates thereby generating more revenue for app developers or related entities.

None of the heretofore disclosed and/or utilized systems or methods provide utilization of a rear side of transparent display screen to advertise and display an advertisement image, while the electronic mobile device is held up in front of the device user. This in such a manner as to is not in transparent mode or the device is next to the user's ear.

Additionally none of the heretofore disclosed and/or utilized systems or methods provide a mobile electronic device with transparent display screen to display reversed images, text or advertisement from an apps to be read from the rear of the electronic mobile device.

Additionally, none of the heretofore disclosed and/or utilized systems or methods provides a mobile electronic device with multiple transparent display screen layers that can use one of the middle layers of transparent display screen to be black/white out, partial or full (used as divider from front and rear display screen) to display image A in the front and image B in the rear at the same time. Image B in the rear of the screen may display selected image, text or advertisement from apps.

Additionally, none of the heretofore disclosed and/or utilized systems or methods provides an electronic mobile device utilizing sensors on a circuit board to display a transparent screen. The electronic mobile device screen may go blank if the device is showing an image on the rear of the transparent screen. Furthermore, the rear side of the transparent display screen may show a message to the user. The message informing the user to turn the device around if the front or intended display side is not correctly facing the device owner.

Additionally, none of the heretofore disclosed and/or utilized systems or methods provides a multiple layered transparent and/or translucent display screen with rear images that may be shown in different colors, patterns or a combination thereof, to alert the device user of proper orientation. This feature may be beneficial for map/speed apps, which show directional symbols, letters or numbers which may be read in reversed manner.

Additionally, none of the heretofore disclosed and/or utilized systems or methods provide an electronic mobile device that is viewed from the front and is in non-transparent mode, having option to black/white out one entire layer (one of the display layer or middle layer) or portion of a screen, thereof. Furthermore, using the display screen above or below the black/white out screen to show different images at the same time, such as advertisement from APP or selected image by the device user.

Additionally, none of the heretofore disclosed and/or utilized systems or methods provide a method of assisting the electronic mobile device user to properly orient the electronic mobile device when it is picked up and the image is only supposed to be seen from the front display screen. For example: directional symbols and letters and numbers which can be read in reverse.

BRIEF SUMMARY OF THE INVENTION

The present disclosure details various enhanced transparent display screens for electronic mobile device and methods of operation using various translucence of transparent display screens.

While the present disclosure is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

In light of the present disclosure, here appears a method for generating a stimulated three-dimensional image on an electronic mobile device.

The method may utilize a plurality of associated transparent display screens as well as a plurality of associated lens selected from a predetermined set of associated cameras for generating perspective views of images.

In some embodiments the may be images are viewable using said electronic mobile devices. In these embodiments, the method may have the additional steps of advertising and screen identification using a mobile transparent screen. These additional steps include stimulating a three-dimensional image view of plurality of objects using a selectable number of transparent display screens associated with an electronic mobile device, whereas the said electronic mobile device comprising a plurality of camera lenses associated with said electronic mobile device by assigning a plurality of camera views to said selectable number of transparent display screens.

Additional the embodiment may include generating a plurality of parallax images associated with said selectable number of transparent display screens by adjusting color contrasts and image depth for stimulating a three-dimensional perception of said plurality of objects.

For gaming and photo applications, the present disclosure responds to "different level of pressure" on touchscreen to access different layers of objects in parallax image or bottom layer of transparent display screen.

In some embodiments, additional step of operating said electronic mobile device as a gaming device displaying gaming images with simulated three-dimensional perceptions may be employed. In this addition, the method may further include the steps of associating a first predetermined one of said selectable number of transparent display screens for operating as a game background showing a back display layer associated with a gaming application. Next, the method may include associating a second predetermined one of said selectable number of transparent display screens for operating as a top transparent display screen.

In some embodiments, the method may further include perceptibly moving predetermined objects associated with said gaming application from said game background to said top transparent display screen while generating a plurality of parallax images associated with said selectable number of transparent display screens by controllably adjusting color contrasts and image depth for simulating a three-dimensional perception of said predetermined objects.

In some embodiments, the steps may continue by further controlling translucence of said plurality of associated transparent display screens to operate over a range of translucence from zero translucence or opaque to full translucence or transparent. Additional the step may include operating a predetermined one of said plurality of associated transparent display screens as a translucent layer of said gaming application over a range of translucence values for producing a backlit perception for providing a plurality of image enhancement functions associated with the display of said gaming application.

In some embodiments, the steps may further controllably adjusting said range of translucence values for adjusting contrast and color perception through said translucent layer of said gaming application. Additionally, controllably adjusting said range of translucence for maintaining a controllable level of privacy during gaming application.

In some embodiments, additional steps may include controllably adjusting display vies from full screen to partial screen images to further enhance gaming application operation.

In some embodiments, enhancing visual display of said plurality of associated transparent display screens by fading in a new simulated three-dimensional image associated with the opening of a new gaming application on a preselected bottom layer transparent display screen while fading away an image associated with an preexisting application on a preselected top layer transparent display screen may be employed. By this additional step, further enhancing image quality by displaying said new simulated three-dimensional image using variations in image qualities from the group comprising additional color contrast depth support, translucent backdrop and/or backlit and background of parallax image for simulating an enhance three-dimensional perception may be employed.

In some embodiments, the steps may further include a step of associating selected ones of said plurality of associated lens views from said selected set of associated cameras with selected ones of said plurality of transparent display screens for controllably adjusting parallax image properties associated with selectable associated lens views.

In some embodiments, the steps may further include a step of placing selected ones of said plurality of transparent display screens in association with an opaque LCD, LED or OLED display for generating further simulated three-dimensional images in association with images displayed on said opaque LCD or LED display.

In some embodiments, the steps may further include a step of associating images for display on selected ones of said plurality of transparent display screens with images on said LCD, LED, or OLED display wherein said transparent display screen images display motion at a differing rate from LCD, LED or OLED display.

In some embodiments, the LCD, LED, or OLED layer may display an image serving as a base or foundational image layer and said images on said selected ones of said plurality of transparent display screens serve as simulated three-dimensional motion images.

In some embodiments, the step of associating a plurality of associated transparent display screens may be formed in a layered bonded monolithic.

In some embodiments, the step of associating said plurality of associated transparent display screens may be formed in a layered formed formation.

BRIEF DESCRIPTION OF THE DRAWINGS

The novel features believed characteristic of the disclosed subject matter will be set forth in any claims that are filed later. The disclosed subject matter itself, however, as well as the preferred mode of use, further objectives, and advantages thereof, will best be understood by reference to the following detailed description of an illustrative embodiment when read in conjunction with the accompany drawings, wherein:

Having thus described the invention in general terms, reference will now be made to the accompanying drawings, which are not necessarily drawn to scale, and wherein:

FIG. 1A and FIG. 1C are perspective views illustrating a flip type electronic mobile device with dual screens, in accordance with one embodiment of the present invention.

FIG. 1B and FIG. 1D are perspective views illustrating a slide type electronic mobile device with dual screens, in accordance with one embodiment of the present invention.

FIGS. 2A-2F illustrates front and rear displays varying translucency of an electronic mobile device, in accordance with one embodiment of the present invention.

Figure 2A:
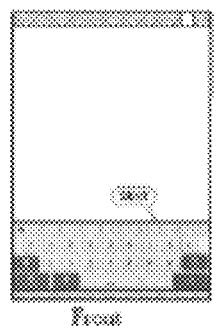
Figure 2B:
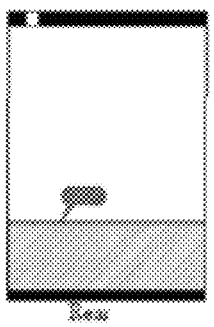
Figure 2C:
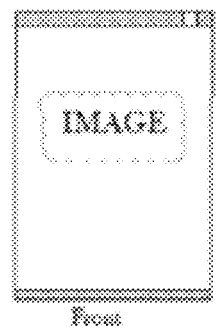
Figure 2D:
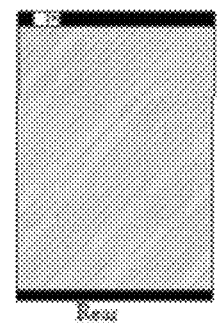
Figure 2E:
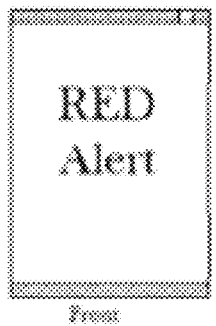
Figure 2F:
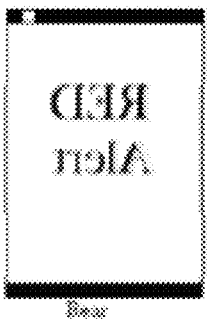
Figure 3A:
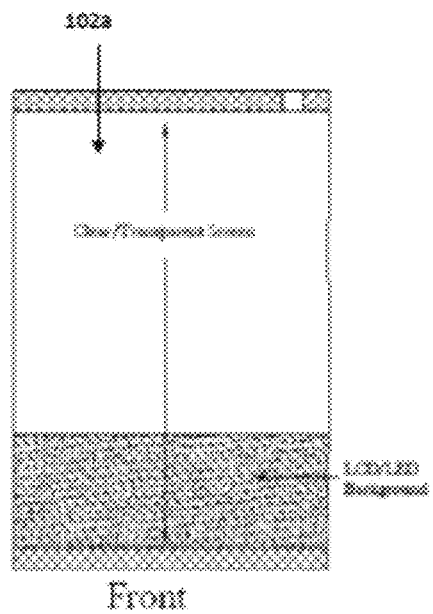
Figure 3B:
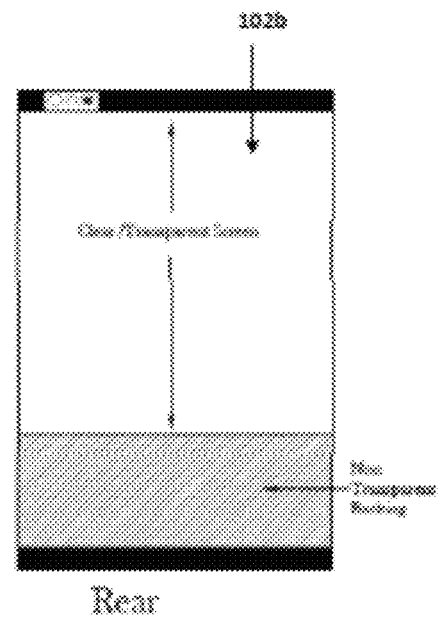

FIG. 3A and FIG. 3B illustrates a front and rear display of a dual screen electronic mobile device, in accordance with one embodiment of the present invention.

Figure 3C:
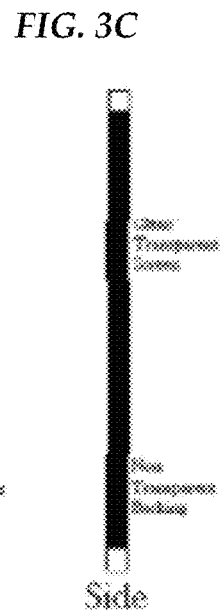

FIG. 3C illustrates a side display of a dual screen electronic mobile device, in accordance with one embodiment of the present invention.

FIGS. 4A-4I illustrates front and rear displays of dual screen electronic mobile devices incorporating parallax imagine, in accordance with one embodiment of the present invention.

Figure 5A:
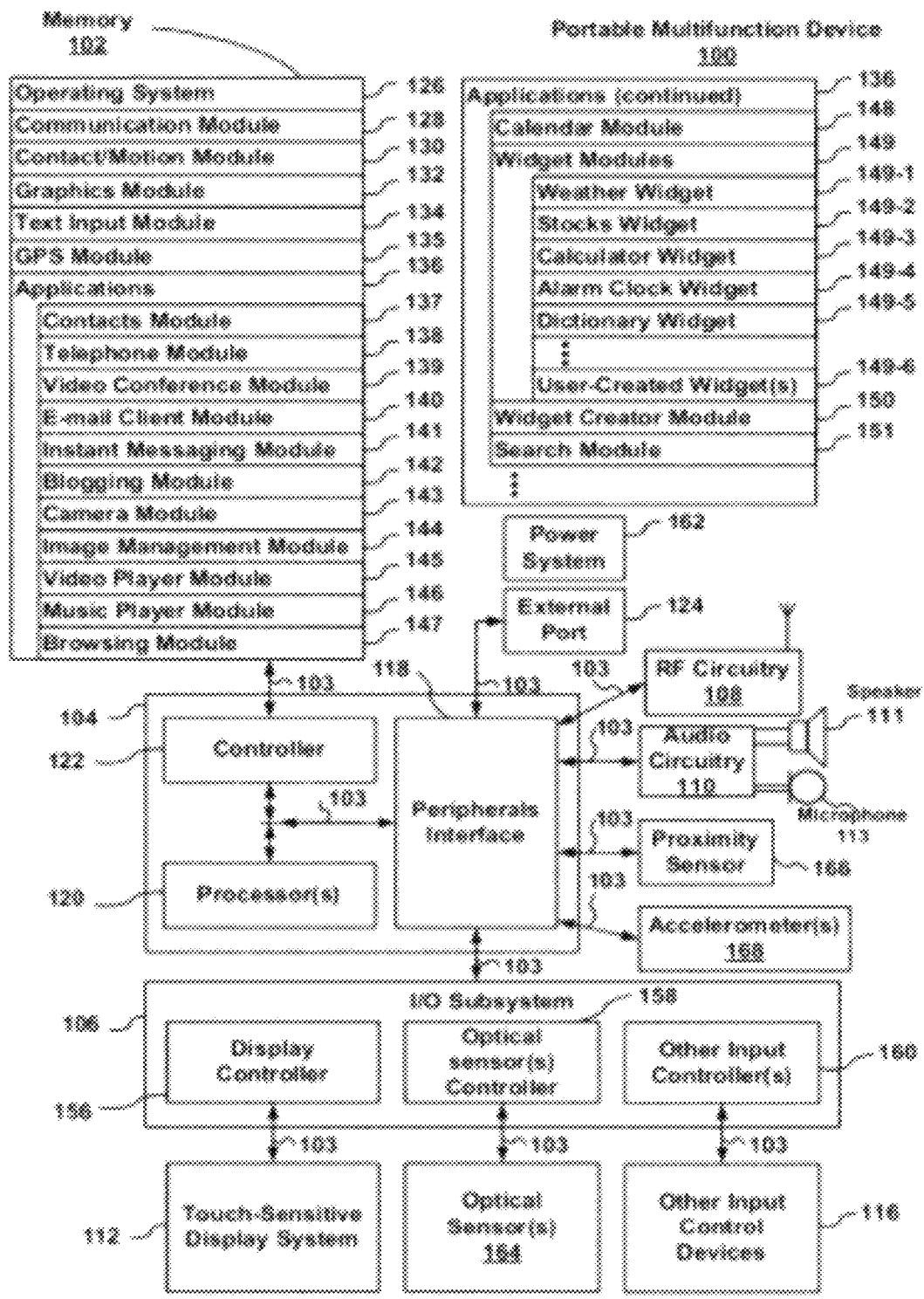
Figure 5B:
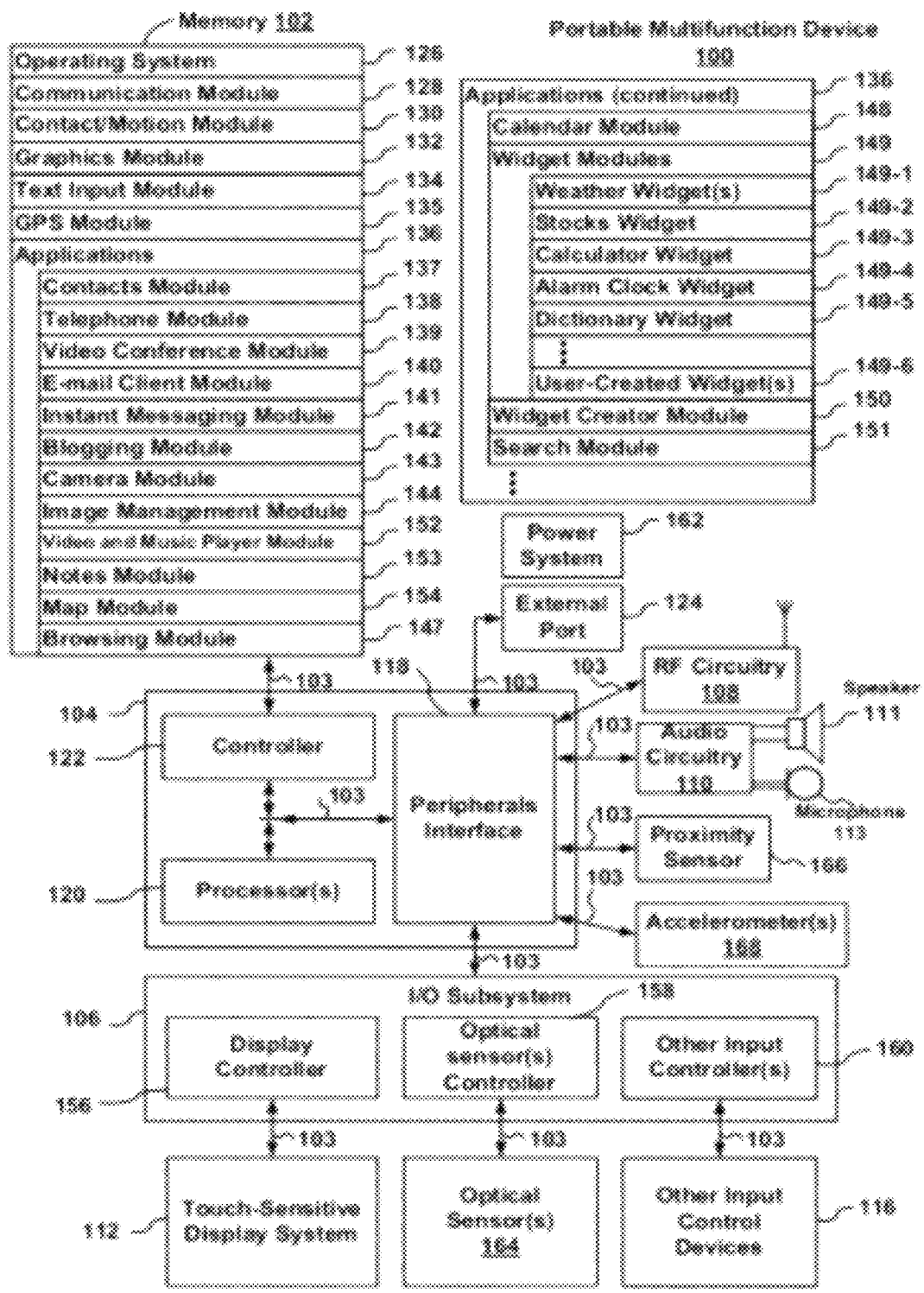
Figure 6:
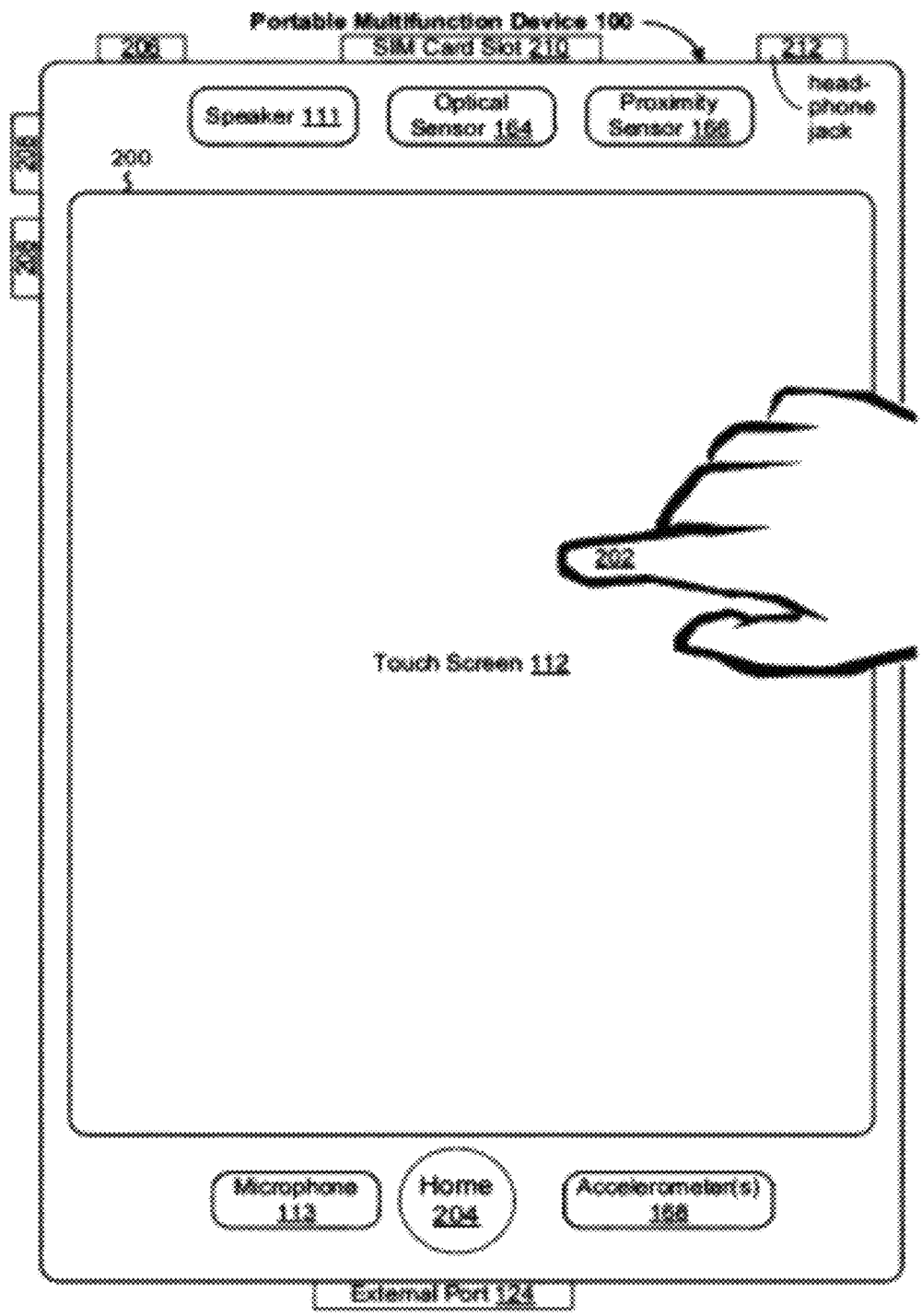

FIGS. 5A and 5B are block diagrams illustrating portable multifunction devices with touch-sensitive displays in accordance with some embodiments; and FIG. 6 illustrates a portable multifunction device 100 having a touch screen 112 in accordance with some embodiments.

DETAILED DESCRIPTION

One or more embodiments of the invention are described below. It should be noted that these and any other embodiments are exemplary and are intended to be illustrative of the invention rather than limiting. While the invention is widely applicable to different types of systems, it is impossible to include all the possible embodiments and contexts of the invention in this disclosure. Upon reading this disclosure, many alternative embodiments of the present invention will be apparent to the persons ordinary skill in the art.

Enhanced transparent display screens for electronic mobile device and methods of operation using various translucence of transparent display screens are described in the forthcoming FIGUREs Images may be generated for display in various forms. Conventionally, images are provided in analog form and are displayed by display devices in two-dimensions. In recent years, images are being provided in digital form for display in two dimensions on display devices having improved resolution, such as high definition display. Even more recently, images capable of being displayed in three-dimensions are being generated.

The present disclosure enables users to view images of three-dimension without the use of special glasses. A display may include a parallax barrier that has a layer of material with series of precision slits. The parallax barrier is placed proximal to a display so that a user's eyes each see a different set of pixels to create a sense of depth through parallax.

Another type of display for viewing three-dimensional images is one that includes lenticular lens. A lenticular lens includes an array of magnifying lenses configured so that when viewed from slightly different angles, different images are magnified.

Parallax barriers, example features that may be dynamically modified include one or more of a number of flits in the parallax barriers, the dimensions of each slit, the spacing between the slits, and the orientation of the slits. Slits of parallax barriers may also be turned on or off in relation to certain regions of the electronic mobile device display screen, such that simultaneous mixed 2D, stereoscopic 3D, and multi-view 3D presentations can be accommodated.

The present disclosure enable app developers to display ads through their apps to app users wherein such ads may be displayed on a front display surface and a rear display surface of an electronic mobile transparent display device. That is, app developers may be able to display ads outside of the present app and onto a rear display surface such that non-users may view the ads. These methods decrease clutter within electronic mobile apps that are caused by ads, and allow more individuals view the ads. Consequently, advertisers may be more likely to pay higher rates thereby generating more revenue for app developers or related entities.

As noted, presently software developers designing electronic mobile apps running on mobile devices can generally only display ads within the confines of the app itself. However, Due to limited screen size of many electronic mobile devices, the constraint increases clutter within the apps making it difficult for users to enjoy the app and forcing ads to be displayed in small and confined areas within the app. This, in turn, decreases the quality and appeal of this form of electronic mobile advertising from the perspective of the advertisers, thereby driving down the economic value of such ads and negatively impacting revenues earned by software developers. Furthermore, revenues earned by software developers are limited because ads are no longer seen by users once an electronic mobile app is closed or shut down.

This disclosure, on the other hand, may empower electronic mobile app developers to display ads to their users as well as non-users wherein the ads are displayed from outside the confines of their mobile apps. This method may decrease clutter due to the ads, while providing an outlet for apps to display ads to their users and non-users and earn revenue from advertisers or ad publishers.

FIG. 1A, FIG. 1B, FIG. 1C and FIG. 1D illustrate electronic mobile device 100 having a dual screen configuration. In some embodiments, including the presently illustrated embodiment, the electronic mobile device 100 may be a portable electronic device, such as a cellular phone. Other electronic devices may also include a cellular phone, a personal data organizer, viewable media player, another computer, or the like. Indeed, in such embodiments, a portable electronic device may include a combination of the functionalities of such devices. In addition, the electronic mobile device 100 may allow a user to connect to and communicate through the Internet or through other networks, such as a local or wide area networks. For example, the electronic mobile device 100 may allow a user to access the Internet and to communicate using e-mail, text messaging, or other forms of electronic communication. In other embodiments, the electronic mobile device 100 may include other models and/or types of electronic devices employing a display, available from any manufacturer. Further the electronic mobile device 100 may include handheld devices (e.g., tablet computers and portable media players).

In certain embodiments, the electronic mobile device 100 may be powered by one or more rechargeable and/or replaceable batteries. Such embodiments may be highly portable, allowing a user to carry the electronic mobile device 100 while traveling, working, and so forth. While certain embodiments of the present disclosure are describe with respect to a portable electronic device, it should be noted that the presently disclosed techniques may be applicable to a wide array of other electronic devices and systems that are configured to render graphical data, such as a desktop computer.

As previously disclosed, the present disclosure may incorporate various types of electronic mobile devices. An electronic mobile device according to an embodiment of the present invention will be divided according to a structure of a display, into an electronic mobile device having a dual display an electronic mobile device having a single display. FIGS. 1A-1D show various types of electronic mobile devices each having a dual display. Each electronic mobile device having the dual display and the single display as shown in FIGS. 1A-1D may be applicable to various types of electronic mobile devices, including folder type, flip type, slide type, bar type, rotating type, swivel type, swing type, watch type, or the like.

Hereinafter, the electronic mobile device having the single or dual display may have a transparent display. In a addition, a non-transparent display may further be provided. The transparent display and the non-transparent display may be configured to be overlapped with each other or be separately provided. That is the single display may be configured as one display module having the transparent display and the non-transparent display being overlapped with each other or be implemented only with the transparent display, whereas the dual display may be configured to have the transparent display and the non-transparent display separately provided.

In addition, in all the embodiments, the transparent display may be defined as a Transparent OLED (TOLED), and the non-transparent display may be defined as the display module or a Liquid Crystal Display (LCD). However, the transparent and non-transparent displays are not limited to the TOLED and the LCD, respectively. Also, the transparent display may be a permeable display having both displayable surface (e.g., inner surface-outer surface, or lower surface-upper surface) as shown in FIGS. 2A-2F and FIGS. 3A and 3B. Further, the embodiments disclosed in the present disclosure may be applied to all types of electronic mobile devices; however, depending on embodiments, a certain type of electronic mobile device may be illustrated, which is appropriate for the sake of explanation.

In the presently illustrated embodiment, the electronic mobile device 100 includes an enclosure or housing 101. The housing 101 may be formed from plastic, metal, composite materials, or other suitable materials, or any combination thereof. The housing 101 may be, for example, a handheld housing for a handheld device. The housing 101 may protect the interior components of the electronic mobile device, such as processors, circuitry, and controllers, among others, from physical damage, and may shield the interior components from electromagnetic interference (EMI). In one embodiment, the housing 101 may include one or more bezels that may support multiple display screens. The housing 101 may be formed in such a way to provide a support structure for the remaining elements illustrated in FIGS. 1A, 1B, 1C and 1D. Additionally, some or all of the housing may be made of transparent or translucent material to allow a user to see through the electronic mobile device.

The front and rear displays 102a, 102b, respectively, may output information process in the electronic mobile device 100. For an example, when the electronic mobile device is operating in a phone call mode, the front and rear displays provides a User Interface or a Graphic User Interface which includes information associated with the call. As another example, the electronic mobile device is in a video call mode or a capturing mode, the front and rear displays may additionally or alternatively display images captured and/or received via the User Interface or the Graphical User Interface.

FIGS. 1A, 1B, 1C and 1D further depict the electronic mobile device having dual screen capabilities. In this instance, the electronic mobile device may have a front display screen 102a and rear display screen 102b. The output information may be displayed on the front display screen 102a and no screen on the rear display screen 102b, as shown in FIGS. 1A, 1B, 1C and 1D.

In one embodiment, the electronic mobile device 100 may be a dual screen device that flips open in a portrait orientation, as shown in FIG. 1A. In this instance, the electronic mobile device 100 may comprise a front display screen 102a and a rear display screen 102b. The user may be able to display images and/or text on the front display screen 102a or the 102b, or a combination of both display screens. In a second aspect, user may display images and/or text on one of the front or rear display screens.

In one embodiment, the electronic mobile device 100 may be a dual screen device that slides open in a portrait orientation, as shown in FIG. 1B. In this instance, the electronic mobile device 100 may comprise a front display screen 102a and a rear display screen 102b. The user may be able to display images and/or text on the front display screen 102a or the 102b, or a combination of both display screens. In a second aspect, user may display images and/or text on one of the front or rear display screens.

In one embodiment, the electronic mobile device 100 may be a dual screen device that flips open in a landscape orientation, as shown in FIG. 1C. In this instance, the electronic mobile device 100 may comprise a front display screen 102a and a rear display screen 102b. The user may be able to display images and/or text on the front display screen 102a or the 102b, or a combination of both display screens. In a second aspect, user may display images and/or text on one of the front or rear display screens.

In one embodiment, the electronic mobile device 100 may be a dual screen device that flips open in a landscape orientation, as shown in FIG. 1D. In this instance, the electronic mobile device 100 may comprise a front display screen 102a and a rear display screen 102b. The user may be able to display images and/or text on the front display screen 102a or the 102b, or a combination of both display screens. In a second aspect, user may display images and/or text on one of the front or rear display screens.

FIGS. 1A and 1C are overviews of a flip type electronic mobile device having a dual transparent display, front display 102a and rear display 102b. According to an embodiment of the present disclosure, which shows an electronic mobile device having variable directions to display information according to a posture of the electronic mobile device. As shown in FIGS. 1A and 1C, a flip type electronic mobile device according to an embodiment of the present invention may be configured such that a TOLED is disposed as the front display 102a and a LCD is disposed as the rear display 102b. Further, the LCD may operate as the front display 102a and the TOLED may operate as the rear display 102b.

Such positions of the TOLED and the LCD may also be changed, and accordingly, their functions as the front display and the rear display may also be changed. For example, under the open position of the flip portion, the TOLED may serve as the front display while the LCD may serve as a rear display. Also, the LCD can display an interactive keypad in one embodiment. In addition, under the closed state of the slide portion of the electronic mobile device 100, if the TOLED independently operates, the operation of the LCD at the main body portion can be blocked such that cannot interrupt the display of the TOLED.

Further, the TOLED and the LCD may be overlapped by a touchpad on any one of their upper or lower surface, so as to be usable as touch screens. Hereinafter, although not separately mentioned in very embodiment of the present disclosure, it is assumed that the TOLED and the LCD function as a touch screen. Also, the flip type electronic mobile device 100 may be configured for its flipping portion to be flipped (closed) or slid unflipped (opened) in a landscape (horizontal) or portrait (vertical) direction, according to its posture. Thus, the electronic mobile device 100 may detect its posture and also rotate information and/or images output on the TOLED or the LCD for output according to the detected portion (orientation).

In addition, FIGS. 1A and 1C is an overview illustrating a method for displaying information when the flipped portion is closed or open in the vertical and horizontal orientation, respectively. In some embodiments, the electronic mobile device 100 may have a dual transparent display according to the present disclosure. In this instance, the electronic mobile device 100 may be configured such that the TOLED is disposed at the flipping portion and the LCD and keypad of the user input unit are disposed at the main body portion. The TOLED may also operate as a main display.

FIGS. 1B and 1D are overviews of a slide type electronic mobile device having a dual transparent display, front display 102a and rear display 102b. According to an embodiment of the present disclosure, which shows an electronic mobile device having variable directions to display information according to a posture of the electronic mobile device. As shown in FIGS. 1B and 1D, a slide type electronic mobile device according to an embodiment of the present invention may be configured such that a TOLED is disposed as the front display 102a and a LCD is disposed as the rear display 102b. Further, the LCD may operate as the front display 102a and the TOLED may operate as the rear display 102b.

Such positions of the TOLED and the LCD may also be changed, and accordingly, their functions as the front display and the rear display may also be changed. For example, under the open position of the slide portion, the TOLED may serve as the front display while the LCD may serve as a rear display. Also, the LCD can display an interactive keypad in one embodiment. In addition, under the closed state of the slide portion of the electronic mobile device 100, if the TOLED independently operates, the operation of the LCD at the main body portion can be blocked such that cannot interrupt the display of the TOLED.

Further, the TOLED and the LCD may be overlapped by a touchpad on any one of their upper or lower surface, so as to be usable as touch screens. Hereinafter, although not separately mentioned in very embodiment of the present disclosure, it is assumed that the TOLED and the LCD function as a touch screen. Also, the slide type electronic mobile device 100 may be configured for its sliding portion to be slid inward (closed) or slid outward (opened) in a landscape (horizontal) or portrait (vertical) direction, according to its posture. Thus, the electronic mobile device 100 may detect its posture and also rotate information and/or images output on the TOLED or the LCD for output according to the detected portion (orientation).

In addition, FIGS. 1B and 1D is an overview illustrating a method for displaying information when the flipped portion is closed or open in the vertical and horizontal orientation, respectively. In some embodiments, the electronic mobile device 100 may have a dual transparent display according to the present disclosure. In this instance, the electronic mobile device 100 may be configured such that the TOLED is disposed at the flipping portion and the LCD and keypad of the user input unit are disposed at the main body portion. The TOLED may also operate as a main display.

FIGS. 3A-3F show variations of the front display screen and the rear display screen views under dual display operation. In some embodiments, the dual display may be a front display 102a being a TOLED and a rear display 102b being a rear display as depicted in FIGS. 3A and 3B and FIGS. 3E and 3F. In this instance, the information of the front display 102a may be viewed as the mirror image of the information on the front display 102a. In some embodiments, the dual display may be a front display 102a being a TOLED and a rear display 102b being an LCD. In this instance, the information on the front display 102a is not viewed by a non-user.

In some embodiments, may adjust the translucence of the front and rear display screen by selectively controlling the front display screen and the rear display screen simultaneously. The translucence may range from greater than zero translucence to full transparence.

Embodiments of the present disclosure may selectively control the front display screen and the rear display screen simultaneously, which may include adjusting the translucence of the front and rear display screen. In these instant embodiments, the translucence may range from zero to 20% translucence. Furthermore, the active display images may be an essentially full screen graphical image or an user interface text image.

As shown in FIGS. 4A-4I depicts varying the translucency of the front display 102a and the rear display 102b. Under these conditions, the front and rear display may display mirror images as illustrated in FIGS. 4A-4D.

Figure 4A:
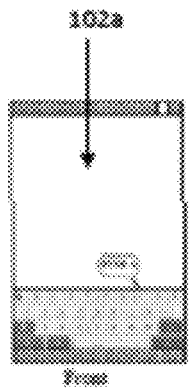
Figure 4B:
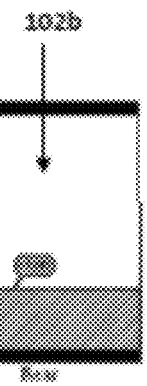
Figure 4C:
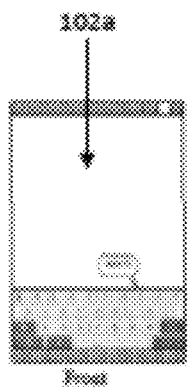
Figure 4D:
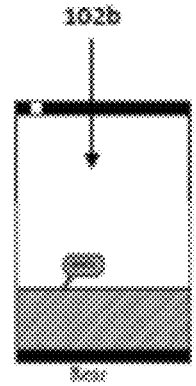
Figure 4E:
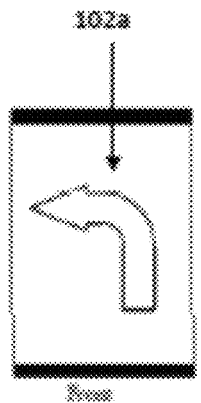
Figure 4F:
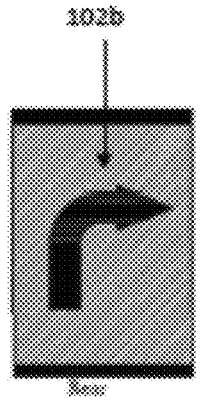
Figure 4G:
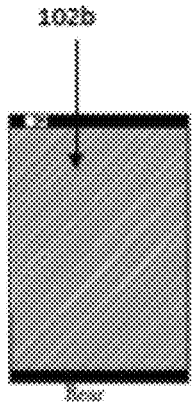

FIGS. 4E-4G illustrate an embodiment of the present invention that may assist user's or non-user's with color blindness. Some people have a color vision deficiency, which means their perception of colors is different from what most others see. The most severe forms of these deficiencies are referred to as color blindness. People with color blindness are not aware of differences among colors that are obvious to others. In the case of color blindness, most individuals will say that a strawberry is red in color. Various cases occur where individuals with color blindness will see the strawberry as orange. Other examples include yellow appearing greener and colors are not as bright. In other cases, read appears black and certain shades of orange, yellow and green appear green. Furthermore, others may perceive red as black and yellow and green appear redder and difficulty lies with distinguishing violet from purple.

In each of the cases of color blindness, FIGS. 4-5 correct this by adding patterns and texture to the digital images. This allows advertisers within the electronic mobile app to effectively advertise the goods to non-users suffering from color blindness.

Figure 4H:
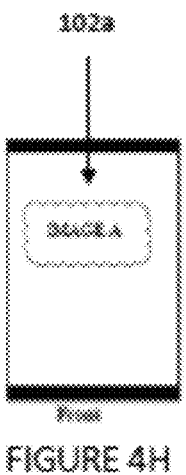
Figure 4I:
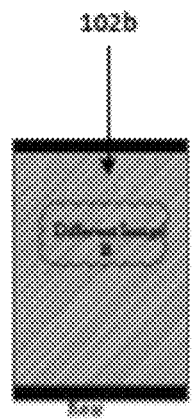

In some embodiments, the front display screen may show different information to the rear display screen, as shown in FIGS. 4H-4I with parallax imagining, as described below.

In addition, the touch screen may be configured to so as to detect input pressure as well as touch input position and touch input area. A proximity sensor (not shown) may be disposed inside the touch screen or near the touch screen. The proximity sensor denotes a sensor for detecting whether there is an object approaching a certain detection surface or existing near the certain detection surface by using a force of an electromagnetic field or infrared rays, without any mechanical contact.

Examples of proximity sensors may include a transmission type photo sensor, a direct reflection type photo sensor, a mirror reflection type sensor, a high frequency oscillation type proximity sensor, a capacitive proximity sensor, a magnetic proximity sensor, an infrared proximity sensor and the like. Also, even with the omission of the proximity sensor mounted, if an electrostatic touch screen is provided, the proximity of a pointer can be detected based upon the change in an electric field due to the proximity of the pointer.

Therefore, if the pointer is located near the touch screen without actually touching the touch screen, the location of the pointer and the gap between the pointer and the touch screen can be detected, Hereinafter, the behavior that the pointer is located near the touch screen so as to be recognized as being located above the touch screen is referred to as a "proximity touch", and the behavior that the pointer is actually contacts the touch screen is referred to as "contact touch". Also, the location at which the proximity touch of the pointer is recognized above the touch screen denotes a location at which the pointer is located perpendicular to the touch screen for the proximity touch of the pointer.

The use of the proximity sensor (not shown) allows the detection of proximity touch and proximity touch patterns, and also allows the output of the touch screen of information related to the detected proximity touch operation and the proximity touch pattern. The touch patterns including proximity touch distance, proximity touch direction, proximity touch speed, proximity touch time, proximity touch location, proximity touch movement state, and the like.

Accordingly, the present disclosure is directed to an electronic mobile device and method of operation thereof that provides for a more convenient stereoscopic user interface.

Another objective of the present disclosure is to provide an electronic mobile device and method of operation thereof, by which user interface may be capable of providing a new visual effect using a 3D object arranged in a virtual 3D space.

A further objective of the present disclosure is to provide an electronic mobile device and method of operation thereof, by which a user interface can be provided via a plurality of layers provided in a 3D space.

An electronic mobile device, according to the present disclosure, includes a display unit configured to display a first image and a second image, a 3D panel unit configured to display the first and second images and 3D images, respectively, and a control unit displaying the first image as a 3D image having a first 3D depth and the second image as a 3D image having a second 3D depth, the control unit controlling the first image to be displayed by being overlapped with the second image.

In another aspect of the present disclosure, an electronic mobile device includes a user input unit configured to receive an input command from a user and a display screen including a liquid crystal display (LCD), light emitting diode display (LED) or an organic light emitting diode display (OLED) and a parallax generating unit provided to a topside of the display screen. The parallax generating unit may change at least one of a propagating direction of a light generated from the display screen and a vibrating direction of the light under the control of the user.

The present disclosure further provides a method of operating the electronic mobile device which includes the step of receiving an input command from a user via an input unit (touchscreen), changing at least one of the propagating direction of a light generated from the display screen and a vibrating direction of the light. Arranging at least one 3D image having a prescribed 3D depth in a virtual stereoscopic pace, generating a first display for changing at least one of a position of a 3D depth of each of the at least one 3D images according to the input of the command from the user, converting the first stereoscopic display to left and right eye images having a prescribed parallax in between, and delivering the left and right eye images to left and right eyes of the user, respectively.

Advantages are rendered through practice of the disclosed various enhanced transparent display screens for electronic mobile device and methods of operation using various translucence of transparent display screens. The disclosed invention empowers advertisers, directly and indirectly, to deliver advertisement to potential customers through target advertisement notifications to users and non-users of the electronic mobile device. Furthermore, the present invention may attract and excite a diverse audience of the electronic mobile device users and non-users with a mobile application that will allow them to receive notifications and alerts on discounts, promotions and savings specific to location of the electronic mobile device. The user of the electronic mobile device may display advertisements on a screen such that non-users are able to view the advertisement. Emergency alerts may be displayed to non-users of the device. Furthermore, advertisements may be tailored to individuals suffering from color-blindness. Furthermore, the dual touch screen display may allow for multi-player games.

U.S. Pat. No. 9,367,093 to Pance, issued on Jun. 14, 2016 describes and claims a "Transparent Electronic Device for displaying images on a transparent display of an electronic device. The display may include one or more display screens as well as a flexible circuit for connecting the display screens with internal circuitry of the electronic device. Furthermore, the display screens may allow for overlaying of images over real world viewable objects, as well as a visible window to be present on an otherwise opaque display screen. Additionally, the display may include active and passive display screens that may be utilized based on images to be displayed. The disclosure of U.S. Pat. No. 9,367,093 is expressly incorporated by reference, as though contained fully herein.

For gaming and photo applications the presently disclosed display has the ability to respond to "different levels of pressure" on the touchscreen display to access different layers of objects in parallax image or bottom layer of transparent display screen.

FIGS. 5A and 5B are block diagrams illustrating portable multifunction devices 100 with touch-sensitive displays 112 in accordance with some embodiments. The touch-sensitive display 112 is sometimes called a "touch screen" for convenience, and may also be known as or called a touch-sensitive display system. The device 100 may include a memory 102 (which may include one or more computer readable storage mediums), a memory controller 122, one or more processing units (CPU's) 120, a peripherals interface 118, RF circuitry 108, audio circuitry 110, a speaker 111, a microphone 113, an input/output (I/O) subsystem 106, other input or control devices 116, and an external port 124. The device 100 may include one or more optical sensors 164. These components may communicate over one or more communication buses or signal lines 103.

It should be appreciated that the device 100 is only one example of a portable multifunction device 100, and that the device 100 may have more or fewer components than shown, may combine two or more components, or a may have a different configuration or arrangement of the components. The various components shown in FIGS. 1A and 1B may be implemented in hardware, software or a combination of both hardware and software, including one or more signal processing and/or application specific integrated circuits.

Memory 102 may include high-speed random access memory and may also include non-volatile memory, such as one or more magnetic disk storage devices, flash memory devices, or other non-volatile solid-state memory devices. Access to memory 102 by other components of the device 100, such as the CPU 120 and the peripherals interface 118, may be controlled by the memory controller 122.

The peripherals interface 118 couples the input and output peripherals of the device to the CPU 120 and memory 102. The one or more processors 120 run or execute various software programs and/or sets of instructions stored in memory 102 to perform various functions for the device 100 and to process data.

In some embodiments, the peripherals interface 118, the CPU 120, and the memory controller 122 may be implemented on a single chip, such as a chip 104. In some other embodiments, they may be implemented on separate chips.

The RF (radio frequency) circuitry 108 receives and sends RF signals, also called electromagnetic signals. The RF circuitry 108 converts electrical signals to/from electromagnetic signals and communicates with communications networks and other communications devices via the electromagnetic signals. The RF circuitry 108 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth.

The RF circuitry 108 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

The audio circuitry 110, the speaker 111, and the microphone 113 provide an audio interface between a user and the device 100. The audio circuitry 110 receives audio data from the peripherals interface 118, converts the audio data to an electrical signal, and transmits the electrical signal to the speaker 111. The speaker 111 converts the electrical signal to human-audible sound waves. The audio circuitry 110 also receives electrical signals converted by the microphone 113 from sound waves. The audio circuitry 110 converts the electrical signal to audio data and transmits the audio data to the peripherals interface 118 for processing. Audio data may be retrieved from and/or transmitted to memory 102 and/or the RF circuitry 108 by the peripherals interface 118. In some embodiments, the audio circuitry 110 also includes a headset jack (e.g. 212, FIG. 2). The headset jack provides an interface between the audio circuitry 110 and removable audio input/output peripherals, such as output-only headphones or a headset with both output (e.g., a headphone for one or both ears) and input (e.g., a microphone).

The I/O subsystem 106 couples input/output peripherals on the device 100, such as the touch screen 112 and other input/control devices 116, to the peripherals interface 118. The I/O subsystem 106 may include a display controller 156 and one or more input controllers 160 for other input or control devices. The one or more input controllers 160 receive/send electrical signals from/to other input or control devices 116. The other input/control devices 116 may include physical buttons (e.g., push buttons, rocker buttons, etc.), dials, slider switches, joysticks, click wheels, and so forth. In some alternate embodiments, input controller(s) 160 may be coupled to any (or none) of the following: a keyboard, infrared port, USB port, and a pointer device such as a mouse. The one or more buttons (e.g., 208, FIG. 2) may include an up/down button for volume control of the speaker 111 and/or the microphone 113. The one or more buttons may include a push button (e.g., 206, FIG. 2). A quick press of the push button may disengage a lock of the touch screen 112 or begin a process that uses gestures on the touch screen to unlock the device, as described in U.S. patent application Ser. No. 11/322,549, "Unlocking a Device by Performing Gestures on an Unlock Image," filed Dec. 23, 2005, which is hereby incorporated by reference in its entirety. A longer press of the push button (e.g., 206) may turn power to the device 100 on or off. The user may be able to customize a functionality of one or more of the buttons. The touch screen 112 is used to implement virtual or soft buttons and one or more soft keyboards.

The touch-sensitive touch screen 112 provides an input interface and an output interface between the device and a user. The display controller 156 receives and/or sends electrical signals from/to the touch screen 112. The touch screen 112 displays visual output to the user. The visual output may include graphics, text, icons, video, and any combination thereof (collectively termed "graphics"). In some embodiments, some or all of the visual output may correspond to user-interface objects, further details of which are described below.

A touch screen 112 has a touch-sensitive surface, sensor or set of sensors that accepts input from the user based on haptic and/or tactile contact. The touch screen 112 and the display controller 156 (along with any associated modules and/or sets of instructions in memory 102) detect contact (and any movement or breaking of the contact) on the touch screen 112 and converts the detected contact into interaction with user-interface objects (e.g., one or more soft keys, icons, web pages or images) that are displayed on the touch screen. In an exemplary embodiment, a point of contact between a touch screen 112 and the user corresponds to a finger of the user.

The touch screen 112 may use LCD (liquid crystal display) technology, or LPD (light emitting polymer display) technology, although other display technologies may be used in other embodiments. The touch screen 112 and the display controller 156 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 112.

A touch-sensitive display in some embodiments of the touch screen 112 may be analogous to the multi-touch sensitive tablets described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in their entirety. However, a touch screen 112 displays visual output from the portable device 100, whereas touch sensitive tablets do not provide visual output.

A touch-sensitive display in some embodiments of the touch screen 112 may be as described in the following applications: (1) U.S. patent application Ser. No. 11/381, 313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228, 758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

The touch screen 112 may have a resolution in excess of 100 dpi. In an exemplary embodiment, the touch screen has a resolution of approximately 160 dpi. The user may make contact with the touch screen 112 using any suitable object or appendage, such as a stylus, a finger, and so forth. In some embodiments, the user interface is designed to work primarily with finger-based contacts and gestures, which are much less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, the device 100 may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from the touch screen 112 or an extension of the touch-sensitive surface formed by the touch screen.

The device 100 also includes a power system 162 for powering the various components. The power system 162 may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

The device 100 may also include one or more optical sensors 164. FIGS. 1A and 1B show an optical sensor coupled to an optical sensor controller 158 in I/O subsystem 106. The optical sensor 164 may include charge-coupled device (CCD) or complementary metal-oxide semiconductor (CMOS) phototransistors. The optical sensor 164 receives light from the environment, projected through one or more lens, and converts the light to data representing an image. In conjunction with an imaging module 143 (also called a camera module), the optical sensor 164 may capture still images or video. In some embodiments, an optical sensor is located on the back of the device 100, opposite the touch screen display 112 on the front of the device, so that the touch screen display may be used as a viewfinder for either still and/or video image acquisition.

In some embodiments, an optical sensor is located on the front of the device so that the user's image may be obtained for videoconferencing while the user views the other video conference participants on the touch screen display. In some embodiments, the position of the optical sensor 164 can be changed by the user (e.g., by rotating the lens and the sensor in the device housing) so that a single optical sensor 164 may be used along with the touch screen display for both video conferencing and still and/or video image acquisition.

The device 100 may also include one or more proximity sensors 166. FIGS. 4A and 4B show a proximity sensor 166 coupled to the peripherals interface 118. Alternately, the proximity sensor 166 may be coupled to an input controller 160 in the I/O subsystem 106. The proximity sensor 166 may perform as described in U.S. patent application Ser. No. 11/241,839, "Proximity Detector In Handheld Device," filed Sep. 30, 2005; Ser. No. 11/240,788, "Proximity Detector In Handheld Device," filed Sep. 30, 2005; Ser. No. 11/620,702, "Using Ambient Light Sensor To Augment Proximity Sensor Output"; Ser. No. 11/586,862, "Automated Response To And Sensing Of User Activity In Portable Devices," filed Oct. 24, 2006; and Ser. No. 11/638,251, "Methods And Systems For Automatic Configuration Of Peripherals," which are hereby incorporated by reference in their entirety. In some embodiments, the proximity sensor turns off and disables the touch screen 112 when the multifunction device is placed near the user's ear (e.g., when the user is making a phone call). In some embodiments, the proximity sensor keeps the screen off when the device is in the user's pocket, purse, or other dark area to prevent unnecessary battery drainage when the device is a locked state.

The device 100 may also include one or more accelerometers 168. FIGS. 4A and 4B show an accelerometer 168 coupled to the peripherals interface 118. Alternately, the accelerometer 168 may be coupled to an input controller 160 in the I/O subsystem 106. The accelerometer 168 may perform as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are which are incorporated by reference in their entirety. In some embodiments, information is displayed on the touch screen display in a portrait view or a landscape view based on an analysis of data received from the one or more accelerometers.

In some embodiments, the software components stored in memory 102 may include an operating system 126, a communication module (or set of instructions) 128, a contact/motion module (or set of instructions) 130, a graphics module (or set of instructions) 132, a text input module (or set of instructions) 134, a Global Positioning System (GPS) module (or set of instructions) 135, and applications (or set of instructions) 136.

The operating system 126 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

The communication module 128 facilitates communication with other devices over one or more external ports 124 and also includes various software components for handling data received by the RF circuitry 108 and/or the external port 124. The external port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with the 30-pin connector used on iPod (trademark of Apple Computer, Inc.) devices.

The contact/motion module 130 may detect contact with the touch screen 112 (in conjunction with the display controller 156) and other touch sensitive devices (e.g., a touchpad or physical click wheel). The contact/motion module 130 includes various software components for performing various operations related to detection of contact, such as determining if contact has occurred, determining if there is movement of the contact and tracking the movement across the touch screen 112, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). In some embodiments, the contact/motion module 130 and the display controller 156 also detects contact on a touchpad. In some embodiments, the contact/motion module 130 and the controller 160 detects contact on a click wheel.

The graphics module 132 includes various known software components for rendering and displaying graphics on the touch screen 112, including components for changing the intensity of graphics that are displayed. As used herein, the term "graphics" includes any object that can be displayed to a user, including without limitation text, web pages, icons (such as user-interface objects including soft keys), digital images, videos, animations and the like. An animation in this context is a display of a sequence of images that gives the appearance of movement, and informs the user of an action that has been performed (such as moving an email message to a folder). In this context, a respective animation that confirms an action by the user of the device typically takes a predefined, finite amount of time, such as an amount of time between 0.2 and 1.0 seconds, or between 0.5 and 2.0 seconds, depending on the context.

The text input module 134, which may be a component of graphics module 132, provides soft keyboards for entering text in various applications (e.g., contacts 137, e-mail 140, IM 141, blogging 142, browser 147, and any other application that needs text input).

The GPS module 135 determines the location of the device and provides this information for use in various applications (e.g., to telephone 138 for use in location-based dialing, to camera 143 and/or blogger 142 as picture/video metadata, and to applications that provide location-based services such as weather widgets, local yellow page widgets, and map/navigation widgets).

The applications 136 may include the following modules (or sets of instructions), or a subset or superset thereof:

a contacts module 137 (sometimes called an address book or contact list);

a telephone module 138;

a video conferencing module 139;

an e-mail client module 140;

an instant messaging (IM) module 141;

a blogging module 142;

a camera module 143 for still and/or video images;

an image management module 144;

a video player module 145;

a music player module 146;

a browser module 147;

a calendar module 148;

widget modules 149, which may include weather widget 149-1, stocks widget 149-2, calculator widget 149-3, alarm clock widget 149-4, dictionary widget 149-5, and other widgets obtained by the user, as well as user-created widgets 149-6;

widget creator module 150 for making user-created widgets 149-6;

search module 151;

video and music player module 152, which merges video player module 145 and music player module 146;

notes module 153; and/or map module 154.

Examples of other applications 136 that may be stored in memory 102 include other word processing applications, JAVA-enabled applications, encryption, digital rights management, voice recognition, and voice replication.

In conjunction with touch screen 112, display controller 156, contact module 130, graphics module 132, and text input module 134, the contacts module 137 may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference 139, e-mail 140, or IM 141; and so forth. Embodiments of user interfaces and associated processes using contacts module 137 are described further below.

In conjunction with RF circuitry 108, audio circuitry 110, speaker 111, microphone 113, touch screen 112, display controller 156, contact module 130, graphics module 132, and text input module 134, the telephone module 138 may be used to enter a sequence of characters corresponding to a telephone number, access one or more telephone numbers in the address book 137, modify a telephone number that has been entered, dial a respective telephone number, conduct a conversation and disconnect or hang up when the conversation is completed. As noted above, the wireless communication may use any of a plurality of communications standards, protocols and technologies. Embodiments of user interfaces and associated processes using telephone module 138 are described further below.

In conjunction with RF circuitry 108, audio circuitry 110, speaker 111, microphone 113, touch screen 112, display controller 156, optical sensor 164, optical sensor controller 158, contact module 130, graphics module 132, text input module 134, contact list 137, and telephone module 138, the videoconferencing module 139 may be used to initiate, conduct, and terminate a video conference between a user and one or more other participants.

In conjunction with RF circuitry 108, touch screen 112, display controller 156, contact module 130, graphics module 132, and text input module 134, the e-mail client module 140 may be used to create, send, receive, and manage e-mail. In conjunction with image management module 144, the e-mail module 140 makes it very easy to create and send e-mails with still or video images taken with camera module 143. Embodiments of user interfaces and associated processes using e-mail module 140 are described further below.

In conjunction with RF circuitry 108, touch screen 112, display controller 156, contact module 130, graphics module 132, and text input module 134, the instant messaging module 141 may be used to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages and to view received instant messages. In some embodiments, transmitted and/or received instant messages may include graphics, photos, audio files, video files and/or other attachments as are supported in a MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS). Embodiments of user interfaces and associated processes using instant messaging module 141 are described further below.

In conjunction with RF circuitry 108, touch screen 112, display controller 156, contact module 130, graphics module 132, text input module 134, image management module 144, and browsing module 147, the blogging module 142 may be used to send text, still images, video, and/or other graphics to a blog (e.g., the user's blog).

In conjunction with touch screen 112, display controller 156, optical sensor(s) 164, optical sensor controller 158, contact module 130, graphics module 132, and image management module 144, the camera module 143 may be used to capture still images or video (including a video stream) and store them into memory 102, modify characteristics of a still image or video, or delete a still image or video from memory 102. Embodiments of user interfaces and associated processes using camera module 143 are described further below.

In conjunction with touch screen 112, display controller 156, contact module 130, graphics module 132, text input module 134, and camera module 143, the image management module 144 may be used to arrange, modify or otherwise manipulate, label, delete, present (e.g., in a digital slide show or album), and store still and/or video images. Embodiments of user interfaces and associated processes using image management module 144 are described further below.

In conjunction with touch screen 112, display controller 156, contact module 130, graphics module 132, audio circuitry 110, and speaker 111, the video player module 145 may be used to display, present or otherwise play back videos (e.g., on the touch screen or on an external, connected display via external port 124). Embodiments of user interfaces and associated processes using video player module 145 are described further below.

In conjunction with touch screen 112, display system controller 156, contact module 130, graphics module 132, audio circuitry 110, speaker 111, RF circuitry 108, and browser module 147, the music player module 146 allows the user to download and play back recorded music and other sound files stored in one or more file formats, such as MP3 or AAC files. In some embodiments, the device 100 may include the functionality of an MP3 player, such as an iPod (trademark of Apple Computer, Inc.). Embodiments of user interfaces and associated processes using music player module 146 are described further below.

In conjunction with RF circuitry 108, touch screen 112, display system controller 156, contact module 130, graphics module 132, and text input module 134, the browser module 147 may be used to browse the Internet, including searching, linking to, receiving, and displaying web pages or portions thereof, as well as attachments and other files linked to web pages. Embodiments of user interfaces and associated processes using browser module 147 are described further below.

In conjunction with RF circuitry 108, touch screen 112, display system controller 156, contact module 130, graphics module 132, text input module 134, e-mail module 140, and browser module 147, the calendar module 148 may be used to create, display, modify, and store calendars and data associated with calendars (e.g., calendar entries, to do lists, etc.). Embodiments of user interfaces and associated processes using calendar module 148 are described further below.

In conjunction with RF circuitry 108, touch screen 112, display system controller 156, contact module 130, graphics module 132, text input module 134, and browser module 147, the widget modules 149 are mini-applications that may be downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display system controller 156, contact module 130, graphics module 132, text input module 134, and browser module 147, the widget creator module 150 may be used by a user to create widgets (e.g., turning a user-specified portion of a web page into a widget).

In conjunction with touch screen 112, display system controller 156, contact module 130, graphics module 132, and text input module 134, the search module 151 may be used to search for text, music, sound, image, video, and/or other files in memory 102 that match one or more search criteria (e.g., one or more user-specified search terms).

In conjunction with touch screen 112, display controller 156, contact module 130, graphics module 132, and text input module 134, the notes module 153 may be used to create and manage notes, to do lists, and the like.

In conjunction with RF circuitry 108, touch screen 112, display system controller 156, contact module 130, graphics module 132, text input module 134, GPS module 135, and browser module 147, the map module 154 may be used to receive, display, modify, and store maps and data associated with maps (e.g., driving directions; data on stores and other points of interest at or near a particular location; and other location-based data).

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. For example, video player module 145 may be combined with music player module 146 into a single module (e.g., video and music player module 152, FIG. 4B). In some embodiments, memory 102 may store a subset of the modules and data structures identified above. Furthermore, memory 102 may store additional modules and data structures not described above.

In some embodiments, the device 100 is a device where operation of a predefined set of functions on the device is performed exclusively through a touch screen 112 and/or a touchpad. By using a touch screen and/or a touchpad as the primary input/control device for operation of the device 100, the number of physical input/control devices (such as push buttons, dials, and the like) on the device 100 may be reduced.

The predefined set of functions that may be performed exclusively through a touch screen and/or a touchpad include navigation between user interfaces. In some embodiments, the touchpad, when touched by the user, navigates the device 100 to a main, home, or root menu from any user interface that may be displayed on the device 100. In such embodiments, the touchpad may be referred to as a "menu button." In some other embodiments, the menu button may be a physical push button or other physical input/control device instead of a touchpad.

FIG. 5 illustrates a portable multifunction device 100 having a touch screen 112 in accordance with some embodiments. The touch screen may display one or more graphics within user interface (UI) 200. In this embodiment, as well as others described below, a user may select one or more of the graphics by making contact or touching the graphics, for example, with one or more fingers 202 (not drawn to scale in the figure). In some embodiments, selection of one or more graphics occurs when the user breaks contact with the one or more graphics. In some embodiments, the contact may include a gesture, such as one or more taps, one or more swipes (from left to right, right to left, upward and/or downward) and/or a rolling of a finger (from right to left, left to right, upward and/or downward) that has made contact with the device 100. In some embodiments, inadvertent contact with a graphic may not select the graphic. For example, a swipe gesture that sweeps over an application icon may not select the corresponding application when the gesture corresponding to selection is a tap.

The device 100 may also include one or more physical buttons, such as "home" or menu button 204. As described previously, the menu button 204 may be used to navigate to any application 136 in a set of applications that may be executed on the device 100. Alternatively, in some embodiments, the menu button is implemented as a soft key in a GUI in touch screen 112.

In one embodiment, the device 100 includes a touch screen 112, a menu button 204, a push button 206 for powering the device on/off and locking the device, volume adjustment button(s) 208, a Subscriber Identity Module (SIM) card slot 210, a head set jack 212, and a docking/charging external port 124. The push button 206 may be used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, the device 100 also may accept verbal input for activation or deactivation of some functions through the microphone 113.

A technical advantage of the present disclosure includes the ability to download a screensaver the provides a powdery or transparent screen image from an online source, such as an App Store. The image could then be applied to the backside of the transparent screen recording according to the particular service that the user makes for a side of the transparent display. This could provide a user with the ability to have a designer appearance to the backside of the transparent display skin according to his own preferences.

Another technical advantage of the present disclosure includes the ability to multiple transparent display screens in layers for a mobile device. As such, it is possible to provide a parallax image from may focus on different objects with in the display screen image.

An emerging trend is the use of multiple camera lenses with a single mobile electronic device. When multiple camera lenses are used for determining an image or aspects of an image, the parallax aspect of the image and the information that can be obtained using the multiple transparent screens and the associated camera provide significantly greater options as to how to perceive something in terms of the texture, color, light characteristics and other aspects relating to a particular object.

The benefits and advantages that may be provided by the present invention has been described above with regard to specific embodiments. These benefits and advantages, and any elements or limitations that may cause them to occur or to become more pronounced are not to be construed as critical, required, or essential features of any of any or all of the claims. As used herein, the singular forms "a", "an", and "the" are intended to include the plural forms as well, unless the context clearly indicates otherwise. It is further understood that the terms "comprises" and/or "comprising" or "includes" and/or including", or any other variation thereof, are intended to be interpreted as nonexclusively including the elements or limitations which follow those terms. Accordingly, a system, method, or other embodiment that comprises a set of elements is not limited to only those elements, and may include other elements not expressly listed or inherent to the claimed embodiment. These terms when used in this specification, specify the presence of stated features, regions, integers, steps, operations, elements, and/or components, but do not preclude the presence or addition of one or more features, regions, integers, steps, operations, elements, components, and/or groups thereof.

What is claimed is:

1. A method for generating a stimulated three-dimensional image on an electronic mobile device comprising:
    a plurality of associated transparent display screens;
    a plurality of associated lens selected from a predetermined set of associated cameras for generating perspective views of images;
    wherein the images are viewable using said electronic mobile devices;
    the method comprising the steps of advertising and screen identification using a mobile transparent screen comprising:
    stimulating a three-dimensional image view of a plurality of objects using a selectable number of transparent display screens associated with an electronic mobile device; said electronic mobile device comprising a plurality of camera lenses associated with said electronic mobile device by assigning a plurality of camera views to said selectable number of transparent display screens;
    generating a plurality of parallax images associated with said selectable number of transparent display screens by adjusting color contrasts and image depth for stimulating a three-dimensional perception of said plurality of objects;
    controlling translucence of said plurality of associated transparent display screens to operate over a range of translucence from zero translucence or opaque to full translucence or transparent;
    operating a predetermined one of said plurality of associated transparent display screens as a translucent layer of a gaming application over a range of translucence values for producing a backlit perception for providing a plurality of image enhancement functions associated with the display of said gaming application.

2. The method of claim 1, further comprising the step of operating said electronic mobile device as a gaming device displaying gaming images with simulated three-dimensional perceptions, the method further comprising the steps of:
    associating a first predetermined one of said selectable number of transparent display screens for operating as a game background showing a back display layer associated with a gaming application;
    associating a second predetermined one of said selectable number of transparent display screens for operating as a top transparent display screen; and
    perceptibly moving predetermined objects associated with said gaming application from said game background to said top transparent display screen while generating a plurality of parallax images associated with said selectable number of transparent display screens by controllably adjusting color contrasts and image depth for simulating a three-dimensional perception of said predetermined objects.

3. The method of claim 1, further comprising the steps of:
    controllably adjusting said range of translucence values for adjusting contrast and color perception through said translucent layer of said gaming application; and
    controllably adjusting said range of translucence for maintaining a controllable level of privacy during gaming application.

4. The method of claim 3, further comprising the step of controllably adjusting display vies from full screen to partial screen images to further enhance gaming application operation.

5. The method of claim 1, further comprising the steps of:
    enhancing visual display of said plurality of associated transparent display screens by fading in a new simulated three-dimensional image associated with the opening of a new gaming application on a preselected bottom layer transparent display screen while fading away an image associated with an pre-existing application on a preselected top layer transparent display screen; and
    enhancing image quality by displaying said new simulated three-dimensional image using variations in image qualities from the group comprising additional color contrast depth
    support, translucent backdrop and/or backlit and background of parallax image for simulating an enhance three-dimensional perception.

6. The method of claim 1, further comprising the step of associating selected ones of said plurality of associated lens views from said selected set of associated cameras with selected ones of said plurality of transparent display screens for controllably adjusting parallax image properties associated with selectable associated lens views.

7. The method of claim 1, further comprising the step of placing selected ones of said plurality of transparent display screens in association with an opaque LCD, LED or OLEO display for generating further simulated three-dimensional images in association with images displayed on said opaque LCD or LED display.

8. The method of claim 7, further comprising the step of associating images for display on selected ones of said plurality of transparent display screens with images on said LCD, LED, or OLEO display wherein said transparent display screen images display motion at a differing rate from LCD, LED or OLEO display.

9. The method of claim 8, wherein said LCD, LED, or OLEO layer displays an image serving as a base or foundational image layer and said images on said selected ones of said plurality of transparent display screens serve as simulated three-dimensional motion images.

10. The method of claim 1, further comprising the step associating said plurality of associated transparent display screens in a layered bonded monolithic formation.

11. The method of claim 1, further comprising the stop associating said plurality of associated transparent display screens in a layered formed formation.

\* \* \* \* \*